US00PP25420P2

(12) United States Plant Patent
Hartman

(10) Patent No.: US PP25,420 P2
(45) Date of Patent: Apr. 7, 2015

(54) ***CALADIUM* PLANT NAMED 'SUMMER BREEZE'**

(50) Latin Name: *Caladium×hortulanum*
Varietal Denomination: Summer Breeze

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 115 days.

(21) Appl. No.: 13/986,547

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Summer Breeze', characterized by its upright and uniformly mounding plant habit; vigorous growth habit and rapid growth rate; fancy-type leaves that are creamy white in color with central pink-colored blush, pink-colored venation and green-colored margins; and good landscape performance.

4 Drawing Sheets

Botanical designation: *Caladium×hortulanum.*
Cultivar denomination: 'SUMMER BREEZE'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Summer Breeze'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2006 in Avon Park, Fla. of *Caladium×hortulanum* 'John Peed', not patented, as the female, or seed, parent with *Caladium×hortulanum* 'Candidum Senior', not patented, as the male, or pollen, parent. The new *Caladium* plant was discovered and selected by the Inventor as a single plant within the progeny of the stated cross-pollination in a controlled outdoor nursery environment in Zolfo Springs, Fla. on September, 2007.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2008 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Summer Breeze'. These characteristics in combination distinguish 'Summer Breeze' as a new and distinct *Caladium* plant:

1. Upright and uniformly mounding plant habit.
2. Vigorous growth habit and rapid growth rate.
3. Fancy-type leaves that are creamy white in color with central pink-colored blush, pink-colored venation and green-colored margins.
4. Good landscape performance.

Plants of the new *Caladium* differ primarily from plants of the female parent, 'John Peed', in leaf color as plants of 'John Peed' have dark green-colored leaves with red-colored venation. In addition, plants of the new *Caladium* and 'John Peed' differ in petiole color as plants of 'John Peed' have dark pink-colored leaf petioles with dark green to almost black-colored stippling, streaks and tessellations.

Plants of the new *Caladium* differ primarily from plants of the male parent, 'Candidum Senior', in the following characteristics:

1. Plants of the new *Caladium* are more compact than plants of 'Candidum Senior'.
2. Plants of the new *Caladium* and 'Candidum Senior' differ in leaf coloration as leaves of plants of 'Candidum Senior' are creamy white to dark green-colored venation and margins.
3. Plants of the *Caladium* and 'Candidum Senior' differ in leaf petiole coloration as leaf petioles of plants of 'Candidum Senior' are dark green to almost black or tan green with dark-colored stippling, streaks and stripes.

Plants of the new *Caladium* can be compared to plants of *Caladium×hortulanum* 'Candidum', not patented. In side-by-side comparisons, plants of the new *Caladium* differed primarily from plants of 'Candidum' in the following characteristics:

1. Plants of the new *Caladium* were more compact than and not as open as plants of 'Candidum'.

2. Plants of the new *Caladium* grew slower than plants of 'Candidum' as plants of the new *Caladium* produced finished plants about one week later than plants of 'Candidum'.
3. Plants of the new *Caladium* and 'Candidum' differed in leaf coloration as leaves of plants of 'Candidum' were white in color with dark green-colored venation.
4. Plants of the new *Caladium* and 'Candidum' differed in leaf petiole coloration as leaf petioles of plants of 'Candidum' were tan green in color with darker-colored stripes.

Plants of the new *Caladium* can be compared to plants of *Caladium×hortulanum* 'White Queen', not patented. In side-by-side comparisons, plants of the new *Caladium* differed primarily from plants of 'White Queen' in the following characteristics:

1. Plants of the new *Caladium* and 'White Queen' differed in leaf coloration as leaves of plants of 'White Queen' were white in color with a uniform pink-colored blush across the entire leaf surface with rose red-colored venation.
2. Plants of the new *Caladium* and 'White Queen' differed in leaf petiole coloration as leaf petioles of plants of 'White Queen' were almost black in color with tan pink-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Summer Breeze' in a 15-cm container and grown in a shadehouse.

The photograph at the top of the second sheet is a comparison view of typical plants of 'Summer Breeze' grown in 15-cm containers; the plant on the left has not had its tuber de-eyed and the plant on the right has had its tuber de-eyed prior to planting.

The photograph at the bottom of the second sheet is a view of typical plants of 'Summer Breeze' grown in an open field.

The photograph at the top of the third sheet is a close-up view of typical freshly-harvested tubers and roots of 'Summer Breeze'.

The photograph at bottom of the third sheet is a close-up view of a typical inflorescence of 'Summer Breeze'.

The photograph at the top of the fourth sheet is a comparison view of typical potted plants of 'Candidum' (left), 'Summer Breeze' (center) and 'White Queen' (right).

The photograph at the bottom of the fourth sheet is a comparison view of typical potted plants of the female parent, 'John Peed' (left), 'Summer Breeze' (center) and the male parent, 'Candidum Senior' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Summer Breeze'.

Parentage:

*Female, or seed, parent.*—*Caladium×hortulanum* 'John Peed', not patented.

*Male, or pollen, parent.*—*Caladium×hortulanum* 'Candidum Senior', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to elliptic in shape. Height: About 3.3 cm. Diameter: About 3.6 cm. Segment height: About 2 cm. Segment diameter: About 1.4 cm. Texture: Thick, starchy; somewhat brittle. Color: Epidermis, freshly-harvested: Close to 199B to 199C and N199B. Epidermis, dried: Close to 200A to 200B. Cortical tissue: Close to 36D. Axillary buds: Close to 37C to 37D. Root description: Thick, fleshy contractile roots; color, close to N155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright and uniformly mounding plant habit; vigorous and dense growth habit; rapid growth rate, potted plants in finished or saleable form in about seven to eight weeks after planting tubers; leaf petioles and leaves arise from one or more growing points on tubers; petioles mostly upright and arching outwardly with development.

*Plant height, from soil level to top of foliar plane, shadehouse-grown potted plants.*—About 24 cm to 32 cm.

*Plant height, from soil level to top of inflorescences, shadehouse-grown potted plants.*—About 24.5 cm.

*Plant diameter or spread, shadehouse-grown potted plants.*—About 37 cm to 42 cm.

*Number of clumps per plant, shadehouse-grown potted plants.*—About two to four from de-eyed tubers.

*Cataphylls, shadehouse-grown potted plants.*—Length: About 4 cm to 6.5 cm. Width: About 1 cm to 1.5 cm. Shape: Wedge-shaped. Apex: Acuminate to acute. Base: Sheathing the stem. Color, outer surface: Close to 159C stippled and streaked with close to N200A and tinged with close to 147C; with development, color becoming closer to 200C to 200D stained with close to 187A. Color, inner surface: Close to 155C.

Foliage description:

*Arrangement and type*.—Alternate; simple; fancy-type.

*Length, shadehouse-grown potted plants*.—About 14 cm to 27 cm.

*Width, shadehouse-grown potted plants, flattened*.—About 10.3 cm to 18 cm.

*Shape*.—Broadly ovate.

*Apex*.—Acute to cuspidate.

*Base*.—Sagittate, peltate.

*Margin*.—Entire; mostly flat with some broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing and fully expanded leaves, upper surface: Background color: Close to 155C; towards the center, blushed with close to 185D; margins, close to 147A. Basal notch: Close to 187B. Venation: Close to 185B to 185C. Developing and fully expanded leaves, lower surface: Background color: Close to 155C; towards the center, faintly tinged with close to 185D; towards the margins, close to 147B and 146B; margins, close to 187A. Basal notch: Close to 187B. Midvein: Close to 54C streaked with close to 185C. Primary venation: Close to 195A tinged with close to 54C; areas surrounding the veins, close to 185C. Secondary venation: Close to 146B.

*Petiole*.—Aspect: Initially upright and straight; with development, leaning outwardly; flexible. Length, shadehouse-grown potted plants: About 18 cm to 22 cm. Diameter, distal, shadehouse-grown potted plants: About 3.5 mm to 4.5 mm. Diameter, proximal, shadehouse-grown potted plants: About 6 mm to 8 mm. Color, shadehouse-grown potted plants: Just below the leaf and petiole junction close to 56C to 56D and 36D tinged with close to 194C to 194D with streaks, close to 185B to 185C; overall, close to 199C to 199D variably tinged with close to 182D and stippled, streaked and tessellated with close to N200A tinged with close to 147B. Wing length, shadehouse-grown potted plants: About 3 cm to 5.5 cm. Wing diameter, shadehouse-grown potted plants: About 8 mm to 10 mm. Wing color, shadehouse-grown potted plants, outer surface: Close to 159C stippled and streaked with close to N200A and tinged with close to 147C. Wing color, shadehouse-grown potted plants, inner surface: Close to N155C; outer surface colors and patterns visible.

Inflorescence description: Inflorescences observed on eleven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Moderately night fragrant; sweet jasmine-like fragrance with camphor-like notes.

*Natural flowering season and flower longevity*.—Plants of the new *Caladium* typically flower during the spring or early summer in central Florida; flowers develop about eleven weeks after growth commences; inflorescences last about three days before fading; inflorescences persistent.

*Spathe*.—Length, overall: About 9.5 cm. Length, distal open portion: About 6.5 cm. Length, proximal closed portion: About 3 cm. Width, distal open portion: About 3.5 cm. Width, at constriction: About 1.1 cm. Width, proximal closed portion: About 2 cm. Shape: Elliptic. Apex: Acuminate. Base: Tapering to the peduncle. Margin: Entire. Texture, front and rear surfaces: Smooth, glabrous. Color, front surface: Distal open portion: Close to 155B to 155C; with development, color becoming closer to 200D. Proximal closed portion: Close to 148C to 148D, proximally tinged with close to 187B, color does not change with development. Color, rear surface: Distal open portion: Close to 155A, 155C and 145C to 145D; towards the apex, close to 145A. Proximal closed portion: Close to 138C and 147C to 147D.

*Spadix*.—Length: About 6.5 cm. Length, male flower zone: About 4.8 cm. Length, sterile zone: About 1.2 cm. Length, female flower zone: About 1.7 cm. Diameter, male flower zone: About 8 mm. Diameter, sterile flower zone: About 7 mm. Diameter, female flower zone: About 8 mm. Shape: Columnar, spindle-shaped. Apex: Obtuse. Base: Obtuse. Aspect: Upright. Color, mature, male zone: Close to 158D. Color, mature, sterile zone: Close to 158D. Color, mature, female zone: Close to 11D. Male flowers: Quantity per spadix: About 165. Shape: Obovate. Height: About 3 mm. Diameter: About 3 mm. Pollen amount: None observed. Female flowers: Quantity per spadix: About 112. Shape: Obovate. Height: About 3 mm. Diameter: About 1.5 mm. Stigma color: Close to 11D. Ovary color: Close to 155D.

*Scape*.—Length: About 24.5 cm. Diameter: About 5 mm. Strength: Sturdy; flexible. Aspect: Mostly erect. Texture: Smooth, glabrous; glaucous. Color: Just below spathe, close to 147C faintly streaked with close to N200A; overall, close to 199D variably tined with close to 182D and variable stippled, streaked and tessellated with close to N200A tinged with close to 147C.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Summer Breeze' as illustrated and described.

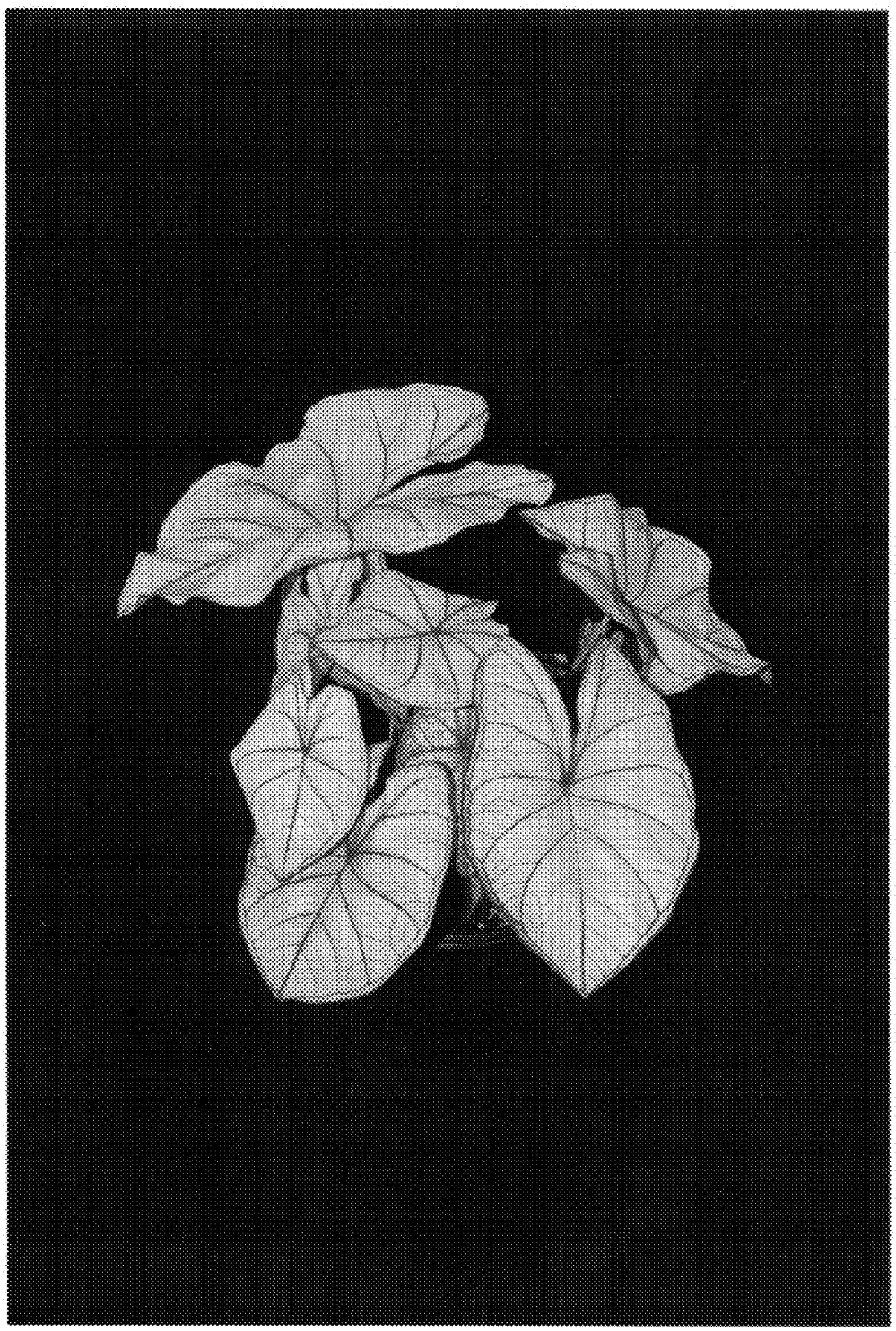

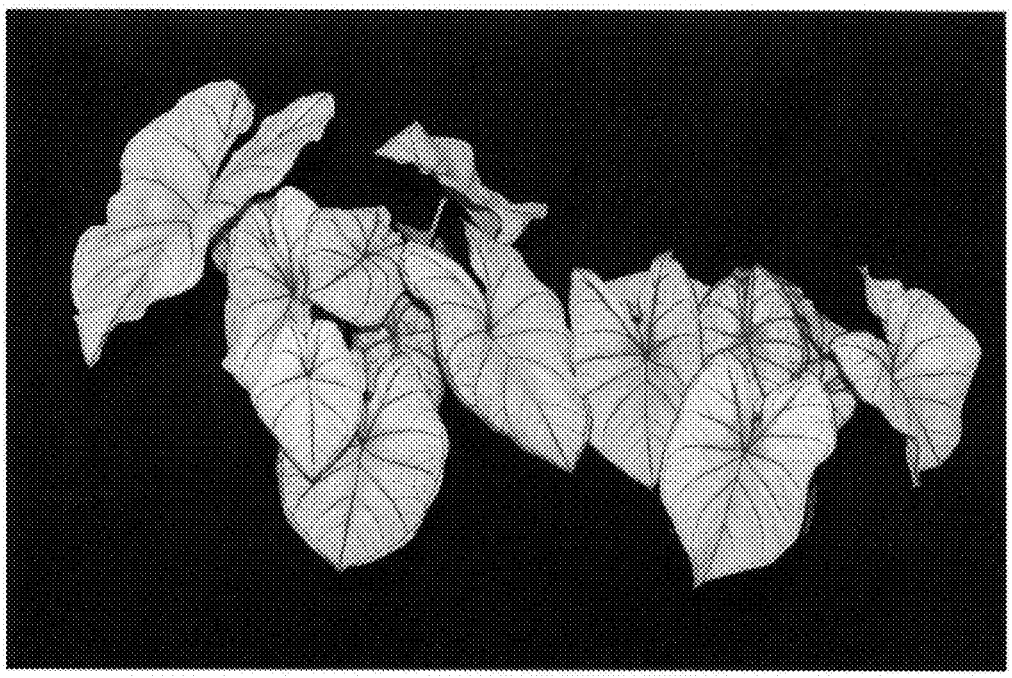
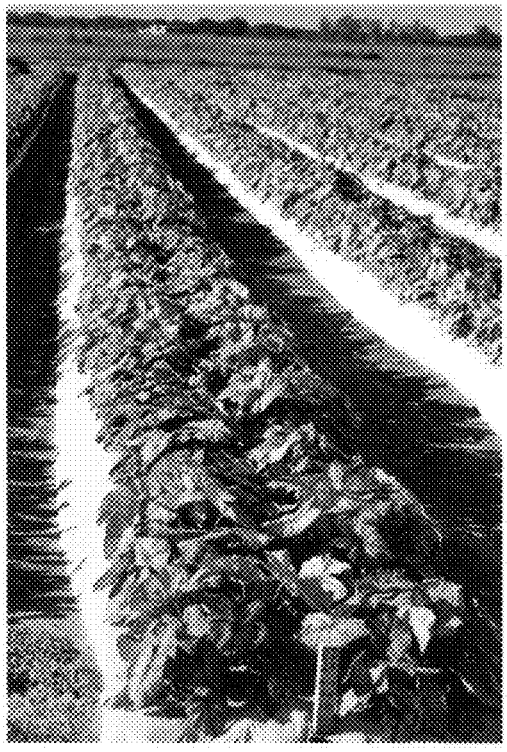

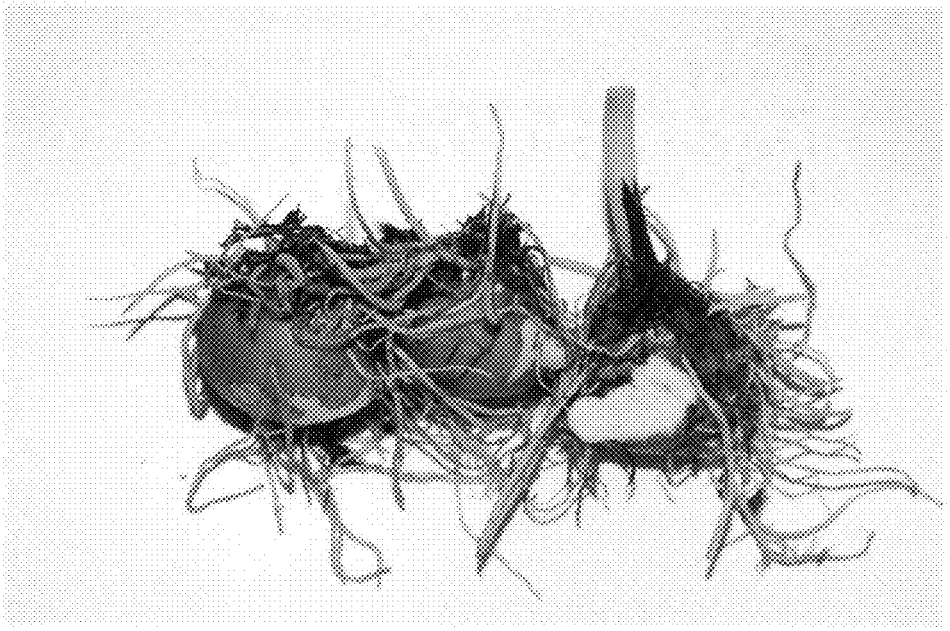
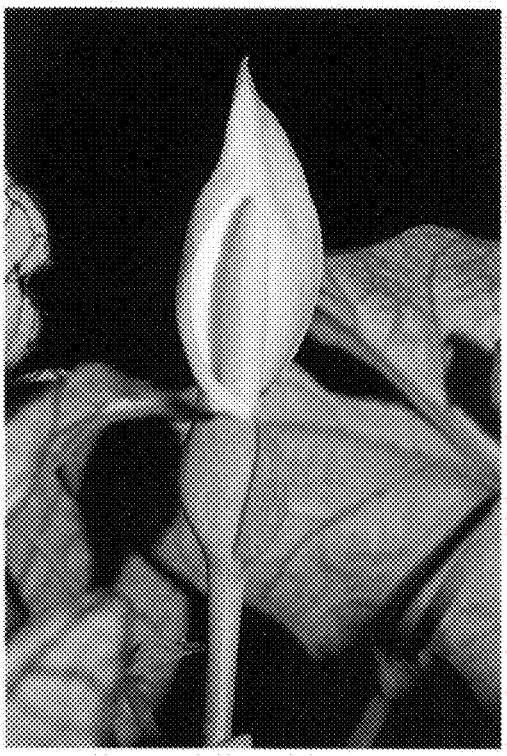

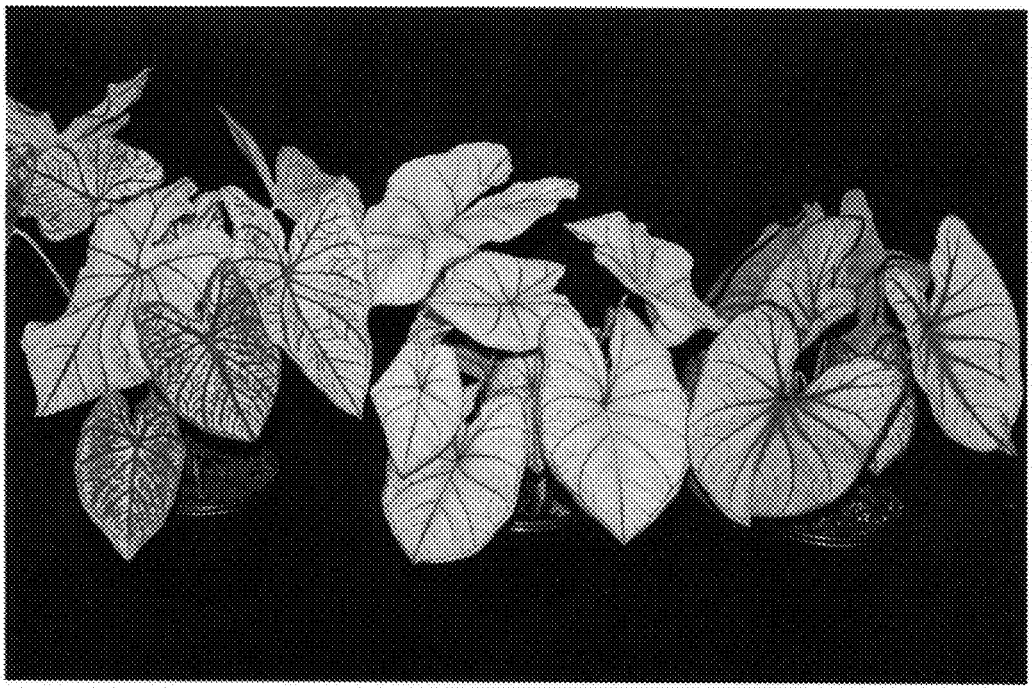
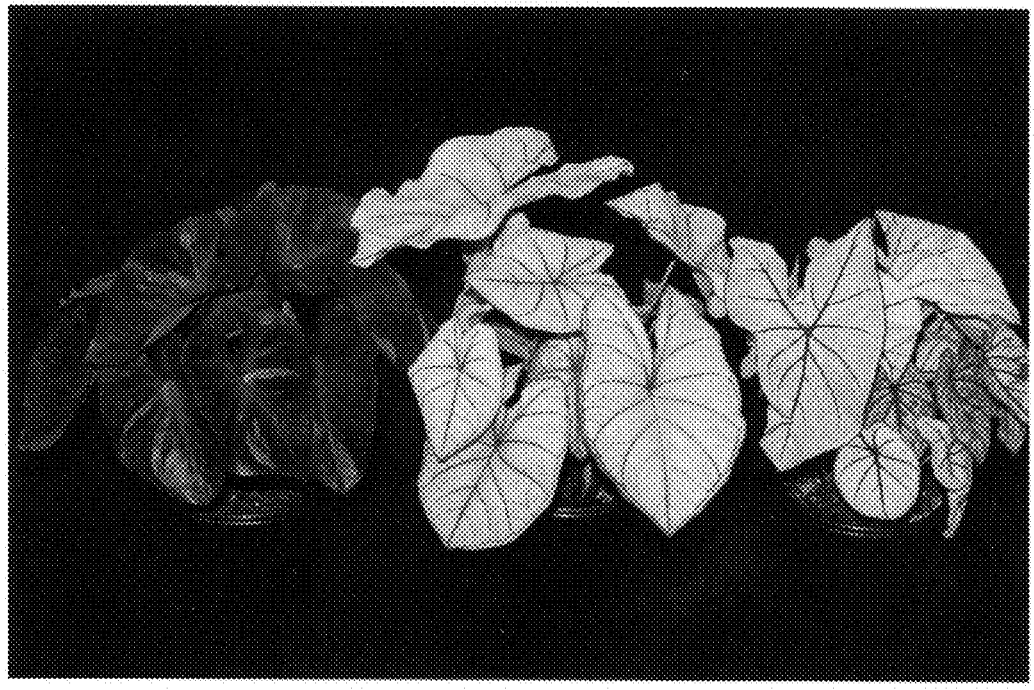

* * * * *